United States Patent [19]

Grisar et al.

[11] Patent Number: 5,500,444
[45] Date of Patent: Mar. 19, 1996

[54] CARDIOPROTECTIVE TOCOPHEROL ANALOGS

[75] Inventors: J. Martin Grisar, Wissembourg; Margaret A. Petty, Strasbourg, both of France; Frank Bolkenius, Kehl, Germany

[73] Assignee: Hoechst Marion Roussel, Inc., Cincinnati, Ohio

[21] Appl. No.: 313,657

[22] Filed: Sep. 27, 1994

Related U.S. Application Data

[63] Continuation of Ser. No. 120,146, Sep. 10, 1993, abandoned, which is a continuation-in-part of Ser. No. 65,058, May 20, 1993, abandoned, which is a continuation of Ser. No. 985,501, Dec. 1, 1992, abandoned, which is a continuation of Ser. No. 840,482, Feb. 24, 1992, abandoned, which is a continuation-in-part of Ser. No. 774,125, Oct. 11, 1991, abandoned, which is a continuation of Ser. No. 686,008, Apr. 12, 1991, abandoned, which is a continuation of Ser. No. 564,670, Aug. 6, 1990, abandoned, which is a continuation of Ser. No. 436,398, Nov. 14, 1989, abandoned.

[51] Int. Cl.$^6$ .......................... A61K 31/35; C07D 311/58
[52] U.S. Cl. ............................ 514/456; 549/407
[58] Field of Search .................... 514/456; 549/407

[56] References Cited

U.S. PATENT DOCUMENTS

| | | |
|---|---|---|
| 3,419,560 | 12/1968 | Bernstein et al. . |
| 3,947,473 | 3/1976 | Scott et al. . |
| 4,153,796 | 5/1979 | Hoehn . |
| 4,214,081 | 7/1990 | Krapcho . |
| 4,237,162 | 12/1990 | Kabbe et al. . |
| 4,321,270 | 3/1982 | Sundeen . |
| 4,617,317 | 10/1986 | Bennett . |
| 4,694,090 | 9/1987 | Shiono et al. . |
| 4,728,650 | 3/1988 | Eziri et al. . |

FOREIGN PATENT DOCUMENTS

| | | |
|---|---|---|
| 0236120 | 9/1987 | European Pat. Off. . |
| 0281261 | 9/1988 | European Pat. Off. . |

OTHER PUBLICATIONS

Shiono et al., Chemical Abstracts 105:226358w (1986).
Shiono et al., Chemical Abstracts 105:197188h (1986).
Shiono et al., Chemical Abstracts 105:97316e (1986).
Sundeen et al., Chemical Abstracts 96:217703y (1982).
Nissen et al., Chemical Abstracts 96:19969b (1982).
Lukovic et al., Brit. J. Pharmacol. 107, p. 370 (1992).
Burger, Medicinal Chem., Interscience Publishers, 2:72–88, (1960).
Akkerman, et al., J. of the Chemical Society Perkin Transactions I, 9:2119–2124 (1979).
Unanue, et al., Text Book of Immunology, Williams & Wilkins, 289–294 (1984).
Koyama, et al., Chemical Abstracts, vol. 3, No. 13, 115639T (1989) and Chem. Pham. Bull., vol. 36, No. 8, 2950–2954 (1988).

*Primary Examiner*—Nicky Chan
*Attorney, Agent, or Firm*—Stephen L. Nesbitt

[57] ABSTRACT

This invention relates to quaternary ammonium salts of certain 2H-1-benzopyran derivatives, to the intermediates and processes useful for their preparation, to their free-radical scavenger and cellular protective properties and to their end-use application as therapeutic agents.

25 Claims, No Drawings

CARDIOPROTECTIVE TOCOPHEROL ANALOGS

CROSS-REFERENCE TO RELATED APPLICATION

This is a continuation of application Ser. No. 08/120,146, filed Sep. 10, 1993 now abandoned, which is a continuation-in-part of application Ser. No. 08/065,058, filed May 20, 1993, now abandoned, which is a continuation of application Ser. No. 07/985,501, filed Dec. 1, 1992, now abandoned, which is a continuation of application Ser. No. 07/840,482, filed Feb. 24, 1992, now abandoned, which is a continuation-in-part of application Ser. No. 07/774,125, filed Oct. 11, 1991, now abandoned, which is a continuation of application Ser. No. 07/686,008, filed Apr. 12, 1991, now abandoned, which is a continuation of application Ser. No. 07/564,670, filed Aug. 6, 1990, now abandoned, which is a continuation of application Ser. No. 07/436,398, filed Nov. 14, 1989, now abandoned, which are herein incorporated by reference.

This invention relates to quaternary ammonium salts of certain 2H-1-benzopyran derivatives, to the intermediates and processes useful for their preparation, to their free-radical scavenger and cellular protective properties and to their end-use application as therapeutic agents.

More specifically this invention relates to quaternary ammonium salt derivatives of the formula

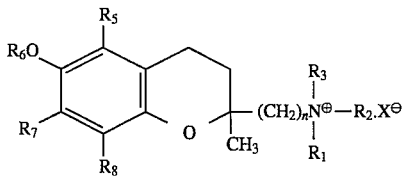

I the (R) and (S) enantiomers and racemic mixtures thereof wherein $R_1$, $R_2$ and $R_3$, each individually is a $C_{1-6}$ lower alkyl, X is a halide or $R_4SO_3^{\ominus}$ with $R_4$ being H, $C_{1-6}$ alkyl, aryl, or aralkyl, $R_5$ is H or $C_{1-6}$ alkyl, $R_6$ is H or $-C(O)R$, R being H or $C_{1-9}$ alkyl, $R_7$ is H or $C_{1-6}$ alkyl, $R_8$ is H or $C_{1-6}$ alkyl and n is an integer of 1 to 6.

As used herein, the moiety $(CH_2)_n$ of Formula I wherein n is an integer of one to six represents a $C_{1-6}$ straight or branched-chain alkylene including such preferred species as methylene, ethylene, propylene, t-butylene, n-butylene, n-hexylene and isopropylene. The term "$C_{1-6}$ alkyl" includes the straight and branched-chain radicals having up to six carbon atoms with methyl, ethyl, propyl, n-butyl, t-butyl, pentyl and hexyl being representative. The term "$-C(O)R$" includes those acyl moieties wherein R is H and $C_{1-9}$ alkyl embracing formyl and the straight and branched-chain alkylcarbonyl moieties having up to ten carbons atoms including methylcarbonyl, ethylcarbonyl, propylcarbonyl, t-butyl-carbonyl and n-hexylcarbonyl as preferred representatives. The term "halide" includes all four halogens with bromo and chloro being preferred. When used, the term "aryl" includes phenyl or its alkylated derivatives with toluyl as the preferred species, aralkyl is benzyl or phenethyl and their alkylated derivatives.

In general, the pharmaceutically acceptable salts include those acid addition salts derived by reaction with such acids as hydrochloric, hydrobromic, sulfuric, nitric or phosphoric acids and such organic carboxylic acids as acetic, propionic, glycolic, maleic, tartaric, citric, salicylic, 2-acetyloxybenzoic acids or organic sulfonic acids such as methanesulfonic, 4-toluenesulfonic and naphthalensulfonic acids.

In general the compounds of Formula I may be prepared by standard chemical processes and techniques analogously known in the art. In practice, the preparation of the compounds of Formula I conveniently utilizes 3,4-dihydro-2,5,7,8-tetramethyl-2H-1-benzopyran-2-ols as starting materials which, for the most part, are known compounds. In those instances wherein any specific starting material is not known then such compounds may readily be prepared using the standard procedures analogously known in the art as well as by applying such processes as would be reasonably expected to produce the desired starting materials.

The preparation of the 3,4-dihydro-2,5,7,8-tetramethyl-2H-1-benzopyran-2-ols and their conversion to the final products of Formula I is depicted in the following reaction scheme.

REACTION SCHEME A:

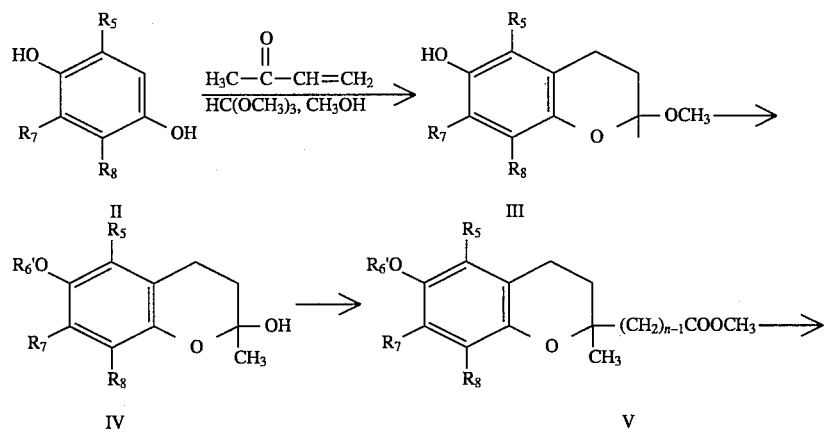

-continued
REACTION SCHEME A:

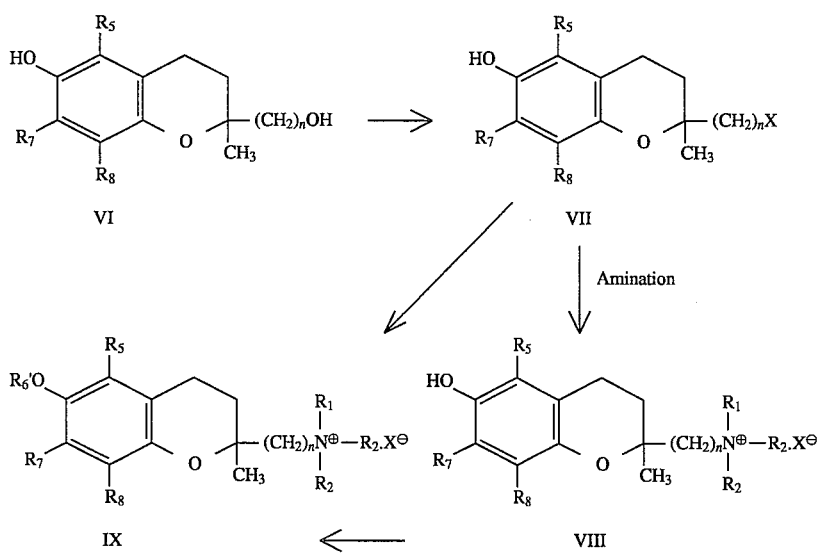

wherein $R_1$, $R_2$, $R_3$, $R_5$, $R_6$, $R_7$ and $R_8$ and n are as previously defined, and $R'_6$ is R—C(O) wherein R is H or $C_{1-9}$ alkyl, and X is an activating moiety, preferably a halide (Cl, Br or I preferred) or )—O—S(0)$_2$R$_4$, with $R_4$ being H, $C_{1-6}$ alkyl, aryl or aralkyl, preferably a tosylate.

The reactions of Scheme A entails the condensation of hydroquinones (II) with 3-butene-2-one in the presence of an acid, preferably sulfuric acid, the condensation being effected in methanol and trimethyl orthoformate. The so-produced dihydrobenzopyrans (III) are then sequentially subjected to acylation and hydrolysis reactions according to standard procedures to yield the hemiketals of Formula (IV). Introduction of the hydroxyalkyl moiety at the 2-position of the compounds of Formula (IV) can be effected by Wittig or Horner type reactions, preferably by reaction of the compounds of Formula (IV) with a trimethylphosphonoester (e.g. trimethylphosphonoacetate) to yield the esters of Formula (V) which are hydrolyzed, and then reduced (preferably with lithium aluminum hydride) to yield the alcohols of Formula (VI). These alcohols may also be formed directly by an acid catalyzed condensation of the hydroquinones (II) with the appropriate vinyl diols of Formulae (IX) and (X),

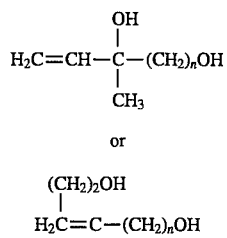

n being as defined above.

Prior to amination, the alcohols of Formula (VI) are first activated by converting the 2-position hydroxyalkyl moieties to either their halides or tosylates (i.e., X' is a halide or a p-toluenesulfonyl radical, preferably Cl or Br or O—S(O)$_2$R$_4$) or other equivalently functioning activating moiety according to standard conditions such as for example reaction of the alcohols with bromotriphenylphosphonium bromide (Ø$_3$PBr$^+$Br$^-$) obtained by reaction of triphenylphosphine with bromine in dichloromethane, or by reacting the alcohols with the appropriate sulfonyl halide (e.g., p-toluene sulfonyl chloride) in the presence of a base according to standard conditions well known in the art. The resulting activated compounds (VII) may be converted to the desired quaternary ammonium derivatives either before or after acylation of the 6-OH moiety. Most preferably, acylation is effected prior to the amination process. Standard amination procedures such as the reaction of the activated moiety with the appropriate trialkylamine under pressure at temperatures of about 90° C. to 150° C., in an inert solvent, preferably butanone, may be used to obtain the quaternary ammonium derivative, and standard acylation procedures such as reaction of the 6-OH moiety with an acid anhydride or acid halide produces the desired alkylcarbonyloxy moiety at the 6-position. Alternatively the compounds of Formula VII (or their 6-alkylcarbonyloxy analogs) may first be converted to their dialkylamino derivatives, as free bases, by reaction with the appropriate dialkylamine according to standard techniques and the resulting 2-dialkylaminoalkylene analogs may be converted to their quaternary ammonium derivatives by reacting the tertiary amines with the appropriate alkylhalides or alkylsulfonates (e.g. R$_2$X wherein X is a halide or O—S(O)$_2$R$_4$. Similarly, acylation at the 6-position may be effected before or after any of the alternate ways to aminate, although as stated it is most preferable that acylation be effected prior to amination.

Further, as there is an asymmetric carbon atom at the 2-position, the compounds may occur as either the R- or the S-enantiomers, or mixtures thereof. The preparation of the individual enantiomeric form may be effected by resolving the acids of Formula (V) by standard and conventional means such as, for example, via the use of diastereomeric salts with optically active amines, or alternatively, by resolving the alcohols (VII) as esters with optically active acids, e.g. L-2,4-MeClC$_6$H$_3$CHMeCOOH (Me representing methyl).

Alternatively, to prepare compounds wherein $R_6$ is H, n is 2 and $R_1$, $R_2$ and $R_3$ are methyl (Reaction Scheme B wherein $R_5$, $R_7$ and $R_8$ are as defined above) an appropriate Formula (IV) compound can be converted to the acids of Formula XI by means of the Wittig-Horner reaction. Sodium tert-butoxide is allowed to react with triethylphosphonoacetate in a suitable solvent such as tetrahydrofuran. A solution of the Formula IV compound is added to the resultant sodium salt and the mixture allowed to react. Without isolation, the intermediate is treated with a suitable base, such as sodium hydroxide (20%), and the Formula XI is then isolated by extraction with toluene, followed by an aqueous wash of the toluene layer, and finally by neutralization of the aqueous phase with an acid such as hydrochloric acid (33%). The solid product is then collected by filtration.

The Formula (XI) compound is converted to an amide of Formula (XII) by formation of the triethylammonium carboxylate with one equivalent of triethylamine employing methylenechloride as the solvent. Subsequent treatment with ethyl chloroformate yields the ethyl ester which upon treatment with dimethylamine gives the dimethylamide of Formula (XII).

The Formula (XII) amide can be converted to the Formula (XIII) amines by, for example, reduction with lithium aluminum hydride ($LiAlH_4$) in tetrahydrofuran. The resulting tertiary amine (XIII) is easily converted to the quaternary ammonium salt in any conventional manner such as by treatment with methyl tosylate.

While Reaction Scheme B illustrates the preparation of compounds of Formula (I) wherein $R_6$ is H and $R_{1-3}$ are each methyl, it will be readily apparent to the skilled artisan that appropriate modification and selection of reactants can readily result in the preparation of other compounds of Formula I. Moreover, preparation of the Formula (I) compounds by the method of Reaction Scheme B offers the additional advantage of allowing the isolation of the individual enantiomers of the desired product. This was readily accomplished for the Formula (I) compound wherein $R_{1-3}$, $R_5$, $R_7$ and $R_8$ are each a methyl, $R_6$ is a hydrogen and n is 2, i.e., 3,4-dehydro-6-hydroxy-2,5,7,8-tetramethyl-2H-1-benzopyran-2-yl)-N,N,N-trimethylethanaminium 4-methyl benzenesulfonate, by reacting the appropriate carboxylic acid of formula (XI) with S-(−)-α-methylbenzylamine which resulted in formation of the ammonium salt which when seeded with the S,S-amine salt allowed for separation by precipitation. The solid precipitate was easily isolated and the resolved S-carboxylic acid used to prepare the (S) enantiomer of the desired Formula (I) compound. The mother liquor containing the R,S-amine salt was treated with dilute acid to regenerate the carboxylic acid which could then be used to regenerate additional R,S starting carboxylic acid by racemization. Example 10 details this overall procedure.

REACTION SCHEME B:

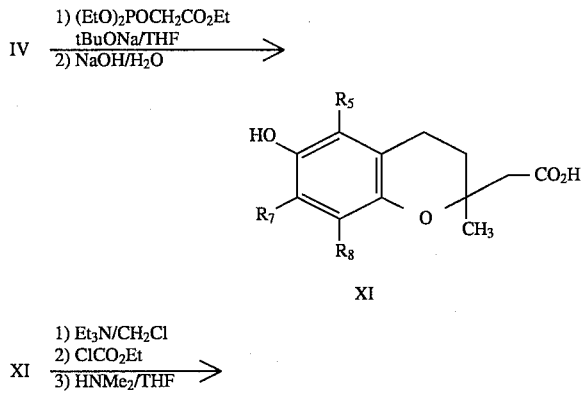

-continued
REACTION SCHEME B:

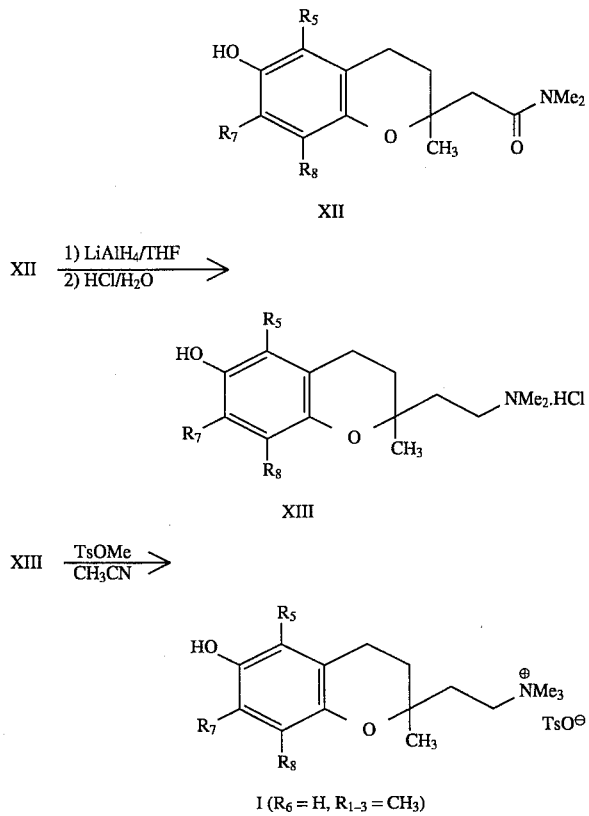

The following examples will serve to illustrate the techniques and processes described herein.

EXAMPLE 1

2-(3,4-Dihydro-6-hydroxy-2,5,7,8-tetramethyl-2H-1-benzopyran-2-yl)ethyl-N,N,N-trimethylammonium bromide

Step A

To 11.0 g (0.042 mol) of triphenylphosphine in 200 ml of dichloromethane is added dropwise a solution of 6.71 g (0.042 mol) of bromine in 50 ml of dichloromethane. The solution is stirred for 30 min at room temperature, then 10.0 g (0.04 mol) of 3,4-dihydro-6-hydroxy-2,5,7,8-tetramethyl-2H-1-benzopyran-2-ethanol (CAS 79907-48-5) is added. The resulting solution is refluxed for 4 hours, allowed to cool overnight, washed with a solution of 15 g of sodium carbonate in 200 ml of water, dried over anhydrous sodium sulfate, filtered and evaporated. The resulting oil is crystallized from methanol to give 9.22 g of 3,4-dihydro-2-(2-bromoethyl)-2,5,7,8-tetramethyl-2H-1-benzopyran-6-ol.

Step B

To 2.90 g of the above bromide in 80 ml of butanone, in a stainless steel bomb is added 6 g of cold (−20° C.) liquid trimethylamine; the bomb is sealed and heated to 120°–125° C. for 60 hours with internal stirring. The bomb is cooled, opened, and its content is transferred to a flask with a solvent. The solvent is evaporated and the residue is recrystallized from ethanol to give 1.99 g of the title compound, m.p. 225° C.

The optically active enantiomers, (R)-2-(3,4-Dihydro-6-hydroxy-2,5,7,8-tetramethyl-2H-1-benzo-pyran-2-yl)ethyl-N,N,N-trimethylammonium bromide and (S)-2-(3,4-Dihydro-6-hydroxy-2,5,7,8-tetramethyl-2H-1-benzo-pyran-2-yl)ethyl-N,N,N-trimethylammonium bromide are obtained by substituting racemic 3,4-dihydro-6-hydroxy-2,5,7,8-tetramethyl-2H-1-benzopyran-3-ethanol with enantiomer R-(CAS 94425-68-0) or S-(CAS-94425-67-9) and by following the procedures of Step A and B for each individual isomer.

In a similar manner, the 4-toluenesulfonate salts of the above compound and its individual optical isomers can be isolated by modification of the procedure of Example 9.

EXAMPLE 2

2-(3,4-Dihydro-2,5,7,8-tetramethyl-6-methylcarbonyloxy-2H-1-benzopyran-2-yl)ethyl-N,N,N-trimethylammonium bromide

Step A

To a solution of 9.22 g (0.029 mol) of 3,4-dihydro-2-(2-bromoethyl)-2,5,7,8-tetramethyl-2H-1-benzo-pyran-6-ol in 60 ml of lutidine is added 30 ml of acetic anhydride. The resulting solution is stirred at room temperature overnight. Water (30 ml) is added and some ice to keep the temperature around 30° C., the mixture is stirred for 30 min, more water and ice are added, the resulting precipitate is collected, washed with water and dried over phosphorus pentoxide under reduced pressure to give 10.0 g of powder. Recrystallization from a mixture of ethyl ether and pentane gives 9.41 g of 3,4-dihydro-2-(2-bromoethyl)-2,5,7,8-tetramethyl-2H-2-benzopyran-6-yl acetate, m.p. 102°–103° C.

Step B

To 6.71 g (0.019 mol) of this acetate in 80 ml of butanone is added about 10 g of cold (–20° C.) liquid trimethylamine. The mixture is stirred and heated to 100°–105° C. in a sealed stainless steel vessel for 60 hours, the solvent is evaporated and the resulting solid is recrystallized twice from ethanol to give 5.18 g of the title compound, m.p. 285° C.

EXAMPLE 3

2-(3,4-Dihydro-6-hydroxy-2,7,8-trimethyl-2H-1-benzo-pyran2yl)ethyl-N,N,N-trimethylammonium bromide Following the procedure described in Example 1, but using 3,4-dihydro-6-hydroxy-2,7,8-trimethyl-2H-1-benzopyran-2-ethanol (CAS 93600-70-5) as starting material, the title compound is obtained.

EXAMPLE 4

2-(3,4-Dihydro-6-hydroxy-2,5,8-trimethyl-2H-1-benzo-pyran-2-yl)ethyl-N,N,N-trimethylammonium bromide Following the procedure described in Example 1, but using 3,4-dihydro-6-hydroxy-2,5,8-trimethyl-2H-1-benzo-pyran-2-ethanol (CAS 93600-69-2) as starting material, the title compound is obtained.

EXAMPLE 5

2-(3,4-Dihydro-6-hydroxy-2,5,7-trimethyl-2H-1-benzo-pyran-2-yl)ethyl-N,N,N-trimethylammonium bromide Following the procedure described in Example 1, but using 3,4-dihydro-6-hydroxy-2,5,7-trimethyl-2H-1-benzopyran-2-ethanol (CAS 93600-68-1) as starting material, the title compound is obtained.

EXAMPLE 6

2-[3,4-Dihydro-2,5,7,8-tetramethyl-6-(1,1-dimethylethyl-carbonyloxy)-2H-1-benzopyran-2-yl]ethyl-N,N,N-trimethylammonium bromide Following the procedure described in Example 2, but substituting acetic anhydride by an equimolar amount of pivaloyl chloride, 3,4-dihydro-2-(2-bromoethyl)-2,5,7,8-tetramethyl-2H-1-benzopyranyl α,α-dimethylpropionate is obtained, which is then converted to the title compound by either the procedure described in Example 2 or that described in Example 9.

EXAMPLE 7

3-(3,4-Dihydro-6-hydroxy-2,5,7,8-tetramethyl-2H-1-benzo-pyran-2-yl)propyl-N,N,N-trimethylammonium bromide Following the procedure described in Example 1, but using 3,4-dihydro-6-hydroxy-2,5,7,8-tetramethyl-2H-1-benzo-pyran-2-propanol (CAS 104568-57-2) as starting material, the title compound is obtained.

EXAMPLE 8

N-Butyl-N-[2-(3,4-dihydro-2,5,7,8-tetramethyl-6-methyl-carbonyloxy-2H-1-benzopyran-2-yl)ethyl]-N,N-dimethylammonium chloride Following the procedure described in Example 9, but substituting methyl p-toluenesulfonate by 1-chlorobutane sulfonate, the title compound is obtained.

EXAMPLE 9

2-(3,4-Dihydro-2,5,7,8-tetramethyl-6-methylcarbonyloxy-2H-1-benzopyran-2-yl)ethyl-N,N,N-trimethylammonium p-toluenesulfonate A mixture of 3.55 g (0.01 mol) of 3,4-dihydro-2-(2-bromoethyl)-2,5,7,8-tetramethyl-2H-benzopyran-6-yl acetate and 2.0 g of liquid dimethylamine in 50 ml of dimethylformamide is stirred at room temperature for 40 hours. Water is added and the product is extracted with ethyl acetate and ethyl ether. The extract is washed with water, dried over anhydrous sodium sulfate, filtered and evaporated. The resulting oil crystallizes from a mixture of ethyl ether and pentane to give 2.05 g of 3,4-dihydro-2-(2-dimethylaminoethyl)-2,5,7,8-tetramethyl-2H-benzopyran-6-yl acetate as the free base.

A solution of 319 mg of the above base and 204 mg (10% excess) of methyl p-toluenesulfonate in 10 ml of acetonitrile is refluxed for 3 hours. The solvent is evaporated and the resulting oil is triturated with ethyl ether. The resulting solid is recrystallized from ethyl acetate to give 302 mg of the title compound, m.p. 108°–111° C.

EXAMPLE 10

(S)-(−)-3,4-Dihydro-6-hydroxy-2,5,7,8-tetramethyl-2H-1-benzopyran-2-acetic acid A mixture of (R,S)-acid of Formula (XI) ($R_5$, $R_7$, $R_8$=$CH_3$) (10.0 g, 37.9 mmol) in i-PrOH (50 mL) was warmed to ca. 80° C. until a solution was obtained. The solution was removed from the heat source and (S)-(=)-α-methylbenzyl-amine (4.6 g, 37.9 mmol) was added in one portion. The solution was then diluted with EtOAc (100 mL), seeded with 90+%ee (S,S)-amine salt, and allowed to cool to room temperature with stirring. After stirring for 16 h, the mixture was filtered. The filter cake was washed with i-PrOH/EtOAc (½ v/v, 2×10 mL), and air-dried to give 5.8 g (40% yield) of the salt as an off-white solid.

The crude salt (5.8 g, 15 mmol) was vigorously stirred in 1M HCl (30 mL) and EtOAc (60 mL). The layers were separated and the aqueous layer was extracted with EtOAc (30 mL). The organic layers were combined and washed sequentially with 20 mL each of 1 M HCl, $H_2O$, brine, dried ($MgSO_4$), and concentrated (40° C./10 torr) to give 3.9 g (98% yield; 84% ee) of (S)-enriched acid of Formula XI as a white solid. mp: 145°–155° C.

Racemization of (R)-(+)-3,4-Dihydro-6-hydroxy-2,5,7,8-tetramethyl-2H-1-benzopyran-2-acetic acid The mother liquor and washings from the filtration of the salt above were combined and concentrated (40° C./20 torr) to 10.1 g of the (R)-enriched acid salt as a thick brown syrup. This syrup was partitioned between 1M HCl (50 mL) and EtOAc (100 mL). The layers were separated and the organic layer was washed successively with 25 mL each of 1M HCl, $H_2O$, and brine, dried ($MgSO_4$) and concentrated (40° C./1 torr) to give 5.8 g (58% yield; 62% ee) of (R)-enriched acid as a light brown solid.

A solution of the enriched (R)-acid (1.0 g, 3.8 mmol) in MeOH (12 mL) and conc. $H_2SO_4$ (2 drops) was heated at 40° C. for 16 h. The solution was cooled to room temperature and partitioned between EtOAc (50 mL) and sat. $NaHCO_3$ (20 mL). The layers were separated and the aqueous layer was extracted with EtOAc (30 mL). The organic layers were combined, washed successively with 20 mL each of sat. $NaHCO_3$, $H_2O$, and brine, dried ($MgSO_4$), and concentrated (40° C./20 torr) to give 1.1 g of enriched (R)-ester of the Formula (XI) carboxylic acid as an orange oil.

This crude enriched (R)-ester (1.1 g) was dissolved in MeOH (8 mL) and treated with NaOMe (2.7 mL of a 25 wt % solution in MeOH, 12 mmol). This solution was heated at reflux for 24 h when $H_2O$ (2 mL) was added to the hot solution and reflux was maintained for an additional 30 min. The solution was cooled to room temperature, 1M HCl (15 mL) was added, and the mixture was stirred vigorously for 1 h. The solid was isolated by filtration, washed with $H_2O$ (2×5 mL), and air-dried overnight to give 0.70 g (70% yield; essentially 1:1/(R):(S), Method A) of (R,S)-acid of Formula (XI) as a brown solid.

(S)-(1)-3,4-Dihydro-6-hydroxy-2,5,7,8-tetramethyl-2H-1-benzopyran-2-(N,N-dimethylacetamide)

A solution of ethyl chloroformate (4.1 mL, 38 mmol) in $CH_2Cl_2$ (68 mL) was cooled to 5° C. and a solution of the (S)-enriched acid (7.50 g, 28.4 mmol, 84% ee) and $Et_3N$ (2.87 g, 28.4 mmol) in $CH_2Cl_2$ (23 mL) was added dropwise over 10 min while maintaining the temperature of the reaction solution below 10° C. The residue in the addition funnel was rinsed with $CH_2Cl_2$ (2×5 mL) into the reaction solution. The reaction solution was stirred at 5°–10 ° C. for an additional 30 min and then treated with $H_2O$ (32 mL). The layers were separated and the aqueous layer was extracted with $CH_2Cl_2$ (30 mL). The organic layers were combined, dried ($MgSO_4$), and concentrated (40° C./20 torr) to give 10.5 g of the mixed anhydride as a viscous yellow oil.

This oil was dissolved in THF (65 mL) and cooled to −10° C. $Me_2NH$ (25 mL of a wt % solution in THF) was added over 15 min while maintaining the temperature of the solution below −5° C. After the addition was complete, the reaction solution was allowed to warm to room temperature overnight. The solution was concentrated (40° C./20 torr) to a white paste. This paste was partitioned between EtOAc (150 mL) and saturated aqueous $NaHCO_3$ (75 mL) by vigorously shaking to dissolve all of the solid. The layers were separated and the aqueous layer was extracted with EtOAc (75 mL). The organic layers were combined, washed successively with saturated aqueous $NaHCO_3$ (75 mL), $H_2O$ (75 mL), and brine (40 mL); then dried ($MgSO_4$) and concentrated (40° C./20 torr) to give 8.0 g (97% yield) of crude enriched (S)-amide of Formula (XII) as a white solid. This solid was dissolved in hot $CH_3CN$ (25 mL), the solution seeded with S-amide (98+% ee), the mixture cooled to 10° C. and filtered. The filter cake was washed with cold $CH_2CN$ (5 mL), air-dried, then dried further in vacuo (50° C./100 tort) to give 6.0 g (73% yeld; 98% ee) of (S)-amide as white prisms. mp: 112° C. (resolidifies) 123+−124° C.

(2S)-(−)-2-(3,4-Dihydro-6,hydroxy-2,5,7,8-tetramethyl-2H-1-benzopyran-2-yl)-N,N,N-trimethylethanaminium 4-methylbenzenesulfonate A mixture of LAH (0.20 g, 5.3 mmol) in THF (18 mL) was warmed to 35° C. and the (S)-amide (1.00 g, 3.4 mmol, 98+%ee) was added in small portions (ca. 0.1 g) over 2 min. The reaction mixture was maintained at 35°–40° C. for 3 h. After cooling to room temperature, the mixture was carefully quenched with saturated aqueous $Na_2SO_4$ (1 mL) and allowed to stir for 1 h. The quenched mixture was filtered through Celite and the filter cake was washed with THF (3×5 mL). The mother liquor and washings were combined and MeOTs (0.70 g, 3.8 mmol) was added in one portion. This reaction solution was heated at 40° C. for 1 h and then concentrated (40° C./1 torr) to give 1.7 g of a brown foam. The foam was dissolved in hot $CH_3CN$/acetone ½ v/v (10 mL) and then t-BuOMe (3.4 mL) was added to the cloud point. The resultant hot hazy mixture was filtered (Celite) and the filter cake was washed with hot $CH_3CN$/acetone ½ v/v (3 mL). Additional t-BuOMe (2 mL) was added to the solution. The solution was seeded and allowed to stand overnight. The crystalline solid was collected by filtration, washed with acetone (3×4 mL), air-dried, then dried further in vacuo (78° C./1 tort) to give 1.2 g (75% yield; 99+% ee) of the desired quaternary salt as peach-colored prisms. mp: 160°–161°;$[\alpha]_D$=−3.90° (c=1.00, 50/50 v/v MeOH/$H_2O$); IR (KBr); $^1$H NMR ($D_2O$); $^{13}$C NMR ($D_2O$) δ147.23, 146.93, 145.02, 142.14, 132.06, 127.99, 126.90, 125.32, 124.79, 121.10, 76.50, 65.32, 55.56, 55.51, 55.46, 34.37, 33.31, 25.47, 23.28, 22.65, 14.74, 13.90, 13.80. MS (E1), m/z (% rel. intensity) 277 (62), 232 (25), 186 (86), 164 (26), 155 (60), 91 (100), 65 (24), 58 (44). Anal. Calcd for $C_{25}H_{37}NO_5S$ (463.6: C, 64.77; H, 8.04; N, 3.02. Found: C, 64.53; H, 8.00; N, 3.05.

EXAMPLE 11

3,4-Dihydro-6-hydroxy-N,,N,N,2,5,7,8-heptamethyl-2H-1-benzopyran-2-ethanaminium 4-methylbenzenesulfonate

Step A 3,4-Dihydro-2-(2-dimethylaminoethyl)-2,5,7,8-tetra-methyl-2H-1-benzopyran-6-ol hydrochloride A mixture of 12.53 g of 3,4-dihydro-2-(2-bromoethyl)-2,5,7,8-tetramethyl-2H-1-benzopyran-6-ol and liquid gaseous dimethylamine in 50 ml of dimethylformamide is stirred at room temperature for 16 hours. Water is added and the product is extracted with ethyl ether. The extract is washed with water, dried over anhydrous sodium sulfate, filtered and evaporated. One equivalent of hydrochloride acid in isopropanol is added and the resulting precipitate is recrystallized twice from isopropanol/water to yield 9.44 g of the title compound, mp 300° C.

Step B

The hydrochloride salt of the compound described in the preceding step is converted to the free base by suspending it in ethyl acetate and a saturated sodium bicarbonate solution and shaking the residue thoroughly several times. The ethyl acetate phase is separated, dried over anhydrous sodium sulfate, filtered, and evaporated. The residue (6.50 g, 0.0227 mol) and 4.37 g (0.032 mol) of methyl p-toluenesulfonate in 60 ml of acetonitrile is stirred at reflux temperature for 4 hours. The salt crystallizes on cooling and is recrystallized from acetonitrile to give 5.20 g (50%) of the title compound, m.p. 160° C. (decomposition); $^1$H-NMR (DMSO-$d_6$) $\delta$ (ppm/TMS) 1.20 (3H, s), 1.76 (1H, t, J=6.8 Hz), 2.00 (1H, m), 2.01 (3H, s), 2.03 (3H, s), 2.06 (3H, s), 2.79 (3H, s), 2.55 (1H, m, J=6.8), 3.06 (9H, s), 3.48 (1H, m), 7.11 (2H, d, J=7.5), 7.44 (1H, s), 7.49 (2H, d, J=7.5); UV (H$_2$)) $\lambda$ max 287 nm (e=7714), 219 (21910).

EXAMPLE 12

Resolution of 3,4-Dihydro-6-hydroxy-2,5,7,8-tetramethyl-2H-1-benzopyran-2-acetic Acid To a hot solution of 132.16 g of the title compound in 700 ml of isopropanol is added 60.59 g of S-(–)-α-methylbenzylamine and 100 ml of ethyl acetate. Slow crystallization overnight in a refrigerator gives somewhat more than half the theoretical amount of crystalline material (checked by evaporating the filtrate to dryness). This material is recrystallized in a like manner three times and the resulting pure diastereomeric salt is converted to free acid by shaking in 200 ml of 2N hydrochloric acid and 400 ml of ethyl acetate. The aqueous phase is separated and extracted with ethyl acetate. The combined organic phase is washed with 2N hydrochloric acid, water, and a saturated sodium chloride solution, dried over anhydrous sodium sulfate, filtered and evaporated to dryness. The resulting solid is recrystallized from ethyl acetate/heptane to give 40.85 g (62%) of the S-(–)-enantiomer of the title compound, $\alpha_D^{25}$=–9.61° (0.95% in MeOH). The enantiomeric purity, as determined by HPLC is ee=99.9%. Elemental analysis was within 0.3% of theory.

The combined filtrates of the above diastereomeric salt crystallizations are evaporated and converted to free acid as described to give 92.02 g of material. It is dissolved in 600 ml of isopropanol and 42.19 g of R-(+)-α-methylbenzylamine is added as well as 200 ml of ethyl acetate. Slow crystallization and two recrystallizations give, after conversion to free acid and one final recrystallization, 41.50 g (63%) of the R-(+)-enantiomer of the title compound, $\alpha_D^{25}$=+9.35° (0.96% in MeOH) ee=99.9%.

It is possible to recover the unresolved balance of material from the filtrates as well as the enantiomeric amines for use in a subsequent resolution.

EXAMPLE 13

2S-(–)- and 2R-(+)-3,4-Dihydro-6-hydroxy-N,N,N,2,5,7,8-heptamethyl-2H-1-benzopyran-2-ethanamium 4-methylbenzenesulfonate

Step 1

To a solution of 4.00 g of the S-(–)-enantiomer of the acid described in the preceding example in 50 ml of dichloromethane, cooled in an ice bath, is added 1.53 g of triethylamine and, dropwise, 45 ml of ethyl chloroformate. The mixture is stirred at 0° C. for 1 hour. Water is added, the organic phase is separated, and the aqueous phase is extracted with dichloromethene. The combined organic phase is dried over anhydrous sodium sulfate, filtered and evaporated to give the mixed anhydride as an oil. This is dissolved in 50 ml of tetrahydrofuran, cooled in ice/methanol, and a solution of 1.37 g of dimethylamine in 20 ml of tetrahydrofuran is added dropwise over 30 minutes. The mixture is stirred for 1 hour and allowed to warm to room temperature. Solvent is evaporated, the residue is taken up in ethyl acetate, washed with 2 N hydrochloric acid and saturated sodium bicarbonate solution, dried over anhydrous sodium sulfate, filtered and evaporated. The resulting product amide is recrystallized from methanol to give 3.1 g (10%) of the 2,S-enantiomer of 3,4-dihydro-6-hydroxy-N,N,2,5,7,8-hexamethyl-2H-1-benzopyran-2-acetamide, m.p. 142° C.

Step 2

A solution of 3.1 g of the amide obtained in the preceding step in 25 ml of dry tetrahydrofuran is added dropwise to a solution of 6.15 g of lithium aluminium hydride in 25 ml of tetrahydrofuran. The mixture is stirred at room temperature for 3 hours. Careful addition of 4.1 ml of water and a solution of 0.68 g of potassium carbonate in 0.63 ml of water and of 1.6 g of sodium sulfate results, after 40 minutes stirring in a precipitate that is removed by filtration and is washed with ethyl acetate. The filtrate is evaporated, the residue is taken up in ethyl acetate, washed with sodium bicarbonate solution, dried over sodium sulfate and filtered. To the filtrate is carefully added 1.2 ml of 33% hydrochloric acid and the resulting precipitate is collected, washed with ethyl acetate and dried to give 3.0 g (90%) of the 2,S-(–), enantiomer of 3,4-dihydro-6-hydroxy-N,N,2,5,7,8-hexamethyl-2H-1-benzopyran-2-alkanamine hyrochloride. m.p.>250° C., $\alpha_D^{25}$=–8.4°.

The 2R-(+)-enanantiomer is prepared analogously and has $\alpha_D^{25}$=+7.6°.

Step 3

The hydrochloride salt of the amine described in the preceding step is converted to free base by shaking a suspension in ethyl acetate with a saturated solution of sodium bicarbonate, separating the organic phase, drying over sodium sulfate, filtering and evaporation of solvent. The residue is dissolved in 20 ml of acetonitrile. 1.74 g of methyl p-toluenesulfonate is added and the solution is refluxed for 2 hours. On cooling, the product crystallizes and is recrystallized from acetonitrile to give 3.5 g (84%) of the S-(−)-enantiomer of the title compound, m.p. 160° C., $\alpha_D^{25}=-4°$ (0.1% in H$_2$O/MeOH 1:1); Anal. calcd. C, 64.77; H, 8.04; N, 3.02; found: C, 64.94; H, 8.10; N, 2.96.

The R-(+)-enantiomer is prepared analogously, m.p. 160° C., $\alpha_D^{25}=4.38°$; Anal. found: C, 65.05; H, 8.08; N, 3.15.

The diastereomeric salts are converted to free base and each resulting enantiomer of 3,4-dihydro-5-hydroxy-N,N,2,5,7,8-hexamethyl-2H-1-benzopyran-2-ethanamine is converted to 3,4-dihydro-6-hydroxy-N,N,N,2,5,7,8-heptamethyl-2H-1-benzopyran-2-ethanaminium 4-methylbenzenesulfonate by treatment with methyl p-toluenesulfonate in acetonitrile as described in method A. The resulting enantiomers had identical properties to those obtained by method A. This establishes the absolute configuration of the enantiomers obtained by either method.

Having described the scope of the compounds of this invention as well as the generic and specific methods for preparing said compounds, the following information describes the utility, and the methods therefor, of the compounds of this invention.

Ischemia folowed by reperfusion causes formation of oxygen-derived free radicals and increased lipid peroxidation and results in tissue injury. Administration of free radical scavengers to animals subjected to ischemia/reperfusion reduces these effects in heart, lung, kidney, pancreas, brain and other tissues.

When the blood supply to parts of the heart muscle is blocked, a myocardial infarct (heart attack) results and the deprived muscle tissue dies with the result of permanent heart damage. If the blood supply can be reestablished within hours after infarction, the heart muscle tissue remains viable and permanent damage can be reduced. This can be accomplished by surgical as well as pharmacologic (thrombolysis) procedures and these processes lead to reperfusion.

In the infarcted reperfused heart an increase in the density of particularly $\beta_2$-receptors in the non-infarcted tissue is apparent, which may reflect a compensatory mechanism to maintain left ventricular function and prevent failure. Treatment with the compound of Example 11 further increased the density of $\beta_2$-receptors and may be an explanation behind the enhanced contractility and cardiac output in rats subjected to myocardial ischemia and reperfusion and treated with the compound of Example 11 (Lukovic et al., 1992, Brit. J. Pharmacol. 107,370P).

Reperfusion is now widely and successfully applied and it has been claimed that fatalities due to myocardial infarction can be reduced by 20–30%. However, reperfusion also poses problems. Oxygen-deprived (ischemic) tissue finds itself in an abnormal state and is vulnerable when suddenly exposed to oxygen-rich blood. This has been termed the "oxygen paradox" and leads to reperfusion damage in the form of cell death. It has been postulated that this damage is due to oxygen-derived free radicals and, in particular, to the superoxide radical, $O_2^-$. Evidence for this hypothesis has been obtained in animal experiments. B. R. Lucchesi and coworkers showed that the enzyme superoxide dismutase, as well as the free radical scavenger N-(mercaptopropionyl) glycine reduce canine myocardial reperfusion injury (Cir. Res., 1984, 54, 277–285; J. Cardiovasc. Pharmacol., 1986, 8, 978–88; Fed. Proc., 1987, 46, 2413–21).

Vitamin E, i.e., α-tocopherol, a well known compound of the formula

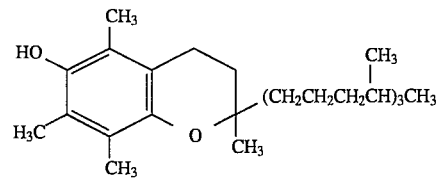

is a natural anti-oxidant that reacts with oxygen-derived free radicals as well as hydrogen peroxide. It has been shown that it is intercalated in lipid membranes and that its biological function is to protect biomembranes against oxidative attack. The anti-oxidant 3,4-dihydro-2,5,7,8-tetramethyl-2H-2-benzopyran-6-ol moiety of α-tocopherol is constantly regenerated by the ubiquitous cytosolic redox systems and for all practical purposes is a permanent membrane constituent that is constantly regenerated.

The compounds of this invention also possess a related or similar 3,4-dihydroxy-2,5,7,8-tetraalkyl-2H-1-benzopyran-2-yl moiety, but the 2-position lipophylic moiety of the α-tocopherol molecule, which is thought to be responsible for its ubiquitous incorporation into biomembranes, is replaced with a hydrophylic moiety to impart a greater affinity for cardiac tissue. Thus, the compounds of this invention are also useful as pharmacologic antioxidants and free radical scavengers and, in particular, as scavengers of superoxide anion radical $O_2^-$. They can be therapeutically employed where reperfusion damage due to oxygen-derived free radicals and hydrogen peroxide causes cell death in tissues. This situation arises when total or partial blockade of blood supply to tissues is removed, either spontaneously (transient ischemia) or by pharmacologic or surgical intervention (thrombolysis, angioplasty, by-pass, organ transplant and the like). Tissues subjected to transient ischemia or reperfusion in various disease states, or by their medical treatment, are those of heart, lung, kidney, pancreas and brain. In particular, the now rapidly increasing practice of pharmacologic thrombolysis, also known as reperfusion, after coronary infarct and stroke, will benefit by prior or concomitant administration of a free radical scavenger such as the compounds of this invention. Similarly, surgical interventions, such as percutaneous transluminal coronary angioplasty, where a dilating balloon is used to increase the luminal diameter in severely occluded atherosclerotic vessels, coronary by-pass operations, and organ transplant surgery create conditions where reperfusion damage due to oxygen-derived radicals takes place and can be reduced by scavengers. Transient ischemia is one of the causative factors that lead to angina pectoris, and thus the compounds of this invention are also useful as antianginal agents.

The process of inflammation is also known to involve the release of superoxide radicals from phagocytic cells which cause some of the symptoms of rheumatoid arthritis and a free radical scavenger, such as the compounds of this invention, is also useful in the treatment of this disease. The compounds may also be useful in the treatment of cancers and of aging since oxygen-derived free radicals have been identified among causative factors. For reviews, see B. Halliwell and C. Gutteridge, Biochem. J., 1984, 219, 1–14; TINS 1985, 22–6. Other inflammatory diseases and conditions which may be treated by the compounds of this invention include ulcerative colitis and inflammatory bowel disease including regional enteritis such as Crohn's Disease and peptic ulcers or ulcers caused by administration of non-steroidal anti-inflammatory agents. An intravenous formulation of the drug can be suitable for the treatment of non-occlusive mesentric ischemia and ischemic colitis.

Inhalation injury of the lungs is typically caused by heat and chemical irritation, and chemical injury is the leading lethal cause of smoke inhalation injury. Smoke inhalation leads to lung injury due to an increase in pulmonary microvasculature and pulmonary edema. This process is accompanied by increased lipid peroxidation in lung tissue. An inhibitor of lipid peroxidation was shown to reduce these symptoms in animals subjected to hot sawdust smoke by Z. Min et al., (J. Med. Cell. PLA, 1990, 5, (2) 176–180). They suggest the use of antioxidants in treatment of smoke inhalation-lung injury, adult respiratory distress syndrome, emphysema and asthma.

Gingivitis and periodontitis are dental diseases due to an inflammatory process. Topical application of a free radical scavenger is reported to reduce the condition in Rhesus monkeys (T. E. Van Dyket et al., Agents and Actions, 1986, 19, 376–7). Thus a mouthwash or toothpaste containing a compound of this invention may be useful in the treatment of these periodontal diseases. Pancreatitis also an inflammatory disease, has also been reported to be amenable to treatment with free radical scavengers (C. Niederau et al., Pancreas, 1991, 6, 282–90).

Reactive oxygen species also play a role in the formation of foam cells in atherosclerotic plaques (reviewed by D. Steinberg et al., Ne Engl. J. Med., 1989, 320, 915–924) and the free radical scavenger probucol has a marked antiatherosclerotic effect in hyperlipidemic rabbits (Carew et al., Proc. Nat. Acad. Sci. USA, 1987, 84, 7725–7729). Degenerative retinal damage and diabetogenic retinopathy have also been listed as target for treatment with free radical scavengers (cf. J. W. Baynes, Diabetes, 1991, 40, 405–412; S. P. Wolff et al., Free Rad. Biol Med., 1991, 10, 339–352).

The compounds may also be useful in the treatment of cancers, and degenerative diseases related to aging, stroke, and head trauma, since oxygen-derived free radicals have been identified among causative fractors. For reviews, see B. Halliwell and C. Gutteridge, Biochem. J., 1984, 219, 1–14; TINS 1985, 22–6. Antioxidants have also been shown to be useful in the treatment of cataracts, Free Rad. Biol. Med., 12:251–161 (1992).

In vitro and in vivo activity of the type of compounds of this invention are illustrated by the following assays which demonstrate the free radical scavenging property, affinity for cardiac tissue and cardioprotective property.

Free Radical Scavenging Property 2-(3,4-dihydro-6-hydroxy-2,5,7,8-tetramethyl-2H-1-benzopyran-2-yl)ethyl-N,N,N-trimethylammonium bromide, described in Example 1, was evaluated for its ability to reduce superoxide radicals in an assay described by H. P. Misra and J. Fridovich, 1972, J. Biol. Chem. 247, 3170–5. In this assay, the rate of autoxidation of 1-epinephrine ($1\times10^{-4}$M) in the presence of EDTA ($1\times10^{-4}$M) at 30° C. is followed spectrophotometrically following the increase of absorbance at 480 mn. 50% inhibition of the autoxidation rate ($ID_{50}$) was obtained at $138\pm14$ μM of the test compound.

For comparison, 3,4-dihydro-6-hydroxy-2,5,7,8-tetramethyl-2H-1-benzopyran-2-carboxylic acid (CAS 53188-07-1) gave $ID_{50}=105\pm8$ μM and d,1-penicillamine (CAS 52-67-15)$ID_{50}=73$μM in parallel experiments. Misra and Fridovich report that bovine superoxide dismutase gave 50% inhibition at 46mg per ml.

In another evaluation, superoxide radicals were generated by 4 mU of xanthine oxidase in the presence of 0.1 mM xanthine and detected by reduction of 40 μM nitro blue tetrazolium to the diformazan dye in a spectrophotometric assay as described by C. Beauchamp and I. Fridovich, (1971) Analyt. Biochem. 44, 276–287. 30 U of superoxide dismutase inhibited this reduction by 90% which, therefore, was due to superoxide radicals. The superoxide radicals were also scavenged by 2-(3,4-dihydro-6-hydroxy-2,5,7,8tetramethyl-2H-1-benzopyrane-2-yl)ethyl-N,N,N-trimethylammonium 4-methylbenzenesulfonate (Compound A), 3,4-dihydro-2-(2-dimethylaminoethyl)-2,5,7,8-tetramethyl-2H-1-benzopyrano-6-ol 4-methylbenzenesulfonate (Compound B) and Trolox (3,4dihydro-6-hydroxy-2,5,7,8-tetramethyl-2H-1-benzopyrane-2-carboxylic acid) to a similar extent with an $IC_{50}=28$ μM. Trolox is a commercial antioxidant and is a known potent superoxide radical scavenger. For comparison, D,L-penicillamine and N-2-mercaptopropionyl glycine at 200 μM scavenged only 14% of the superoxide radicals. Neither of the scavengers inhibited xanthine oxidase, when tested at 200 μM.

Affinity for cardiac tissue

Following the procedure described in Example 9, but using $^{14}$C-methyl p-toluenesulfonate in place of "cold material", $^{14}$C-labelled 2-(3,4-dihydro-2,5,7,8-tetramethyl-6-methylcarbonyloxy-2H-1-benzopyranan-2-yl)ethyl-N,N,N-tri-$^{14}$C-methylammonium p-toluenesulfonate was synthesized. The preparation was diluted with "cold material" to 11.74 μCi/mg base.

24 rats were given 0.91 mg base/kg by intravenous route (by canula into the jugular vein). The animals were sacrificed in groups of 3 at the time periods indicated in Table I. Immediately before sacrifice a 0.5 ml blood sample was taken from an indwelling catheter in the carotid artery. The hearts were removed, blotted and weighed. The samples of tissue and blood were solubiized with Luma Solve (a quaternary ammonium hydroxide preparation) and radioactivity was determined in a scintillation counter.

The results are shown in Table I.

TABLE I

| Time after administration | ng equiv/ g heart | ng equiv/ ml blood | Ratio heart/blood |
| --- | --- | --- | --- |
| 5 min | 1.591 ± 0.22 | 0.434 ± 0.351 | 3.05 ± 1.46 |
| 15 min | 1.728 ± 0.422 | 0.590 ± 0.295 | 6.90 ± 8.34 |
| 30 min | 1.905 ± 0.278 | 0.124 ± 0.032 | 17.33 ± 5.42 |
| 1 hour | 2.092 ± 0.406 | 0.096 ± 0.008 | 20.09 ± 2.54 |
| 2 hours | 1.395 ± 0.042 | 0.086 ± 0.041 | 21.90 ± 3.56 |
| 4 hours | 1.253 ± 0.248 | 0.054 ± 0.013 | 27.15 ± 4.30 |
| 6 hours | 0.863 ± 0.067 | 0.048 ± 0.007 | 18.62 ± 2.77 |
| 8 hours | 0.652 ± 0.116 | 0.048 ± 0.012 | 15.12 ± 2.69 |

It can be seen that the test compound has a marked affinity for heart tissue. The ratio of radioactivity per g of heart tissue to radioactivity per ml of blood increased with time to reach a maximum of 27.15 at 4 h. Even after 8 h the concentration of drug in heart tissue remains elevated (0.65 μg equiv/g).

Cardioprotective effects 2-(3,4-Dihydro-2,5,7,8-tetramethyl-6-methylcarbonyloxy- 2H-1-benzopyran-2-yl)ethyl-N,N,N-trimethylammonium bromide was evaluated in ligation-induced infarcted and reperfused rats as follows. One of two groups of rats was infused intravenously with a solution of test compound in saline at a rate of 2.3 ml/h (10 mg/kg/h). The control group was infused with saline at the same rate. After 10 min of drug infusion, coronary arteries were ligated surgically for 60 min, ligation was loosened to allow reperfusion for 30 min. The ligation was retied and a dye (Evans Blue) was injected. The animals were sacrificed and the heart ventricles were removed and weighed. The unstained tissue was dissected and weighed; this represents the "area at risk", i.e. the area that was deprived of blood supply by ligation. To determine the infarcted area, the tissue was incubated with 2,3,5-triphenyltetrazolium chloride. Infarcted tissue became light colored and could be dissected and weighed. Thus, for each rat that survived the ligation a measurement of "area at risk" and of "infarcted area" was obtained and the ratio was calculated as given in Tables II and III.

TABLE II

| Control Group | | | | |
|---|---|---|---|---|
| Rat No. | Total Ventr. wt., g. | Tissue at risk, mg | Infarcted tissue, mg | Ratio % |
| 1 | 1.445 | 196 | 51 | 25.7 |
| 2 | 1.362 | 383 | 200 | 52.3 |
| 3 | 1.428 | 277 | 152 | 54.6 |
| 4 | 1.470 | 244 | 232 | 95.2 |
| 5 | 1.359 | 272 | 323 | 119 |
| 6 | 1.530 | 452 | 432 | 95.6 |
| 7 | 1.220 | 303 | 339 | 112 |
| 8 | 1.520 | 188 | 173 | 93.5 |
| 9 | 1.133 | 78 | 80 | 102.6 |
| | | | average | 83.31 |
| | | | standard deviation | 31.72 |

TABLE III

| Treated Group (10 mg/kg/h) | | | | |
|---|---|---|---|---|
| Rat No. | Total Ventr. wt., g. | Tissue at risk, mg | Infarcted tissue, mg | Ratio % |
| 1 | 1.381 | 307 | 299 | 97.5 |
| 2 | 1.237 | 255 | 39 | 15.5 |
| 3 | 1.336 | 176 | 33 | 18.9 |
| 4 | 1.197 | 381 | 247 | 64.8 |
| 5 | 1.321 | 310 | 193 | 62.1 |
| 6 | 1.203 | 207 | 134 | 64.5 |
| 7 | 1.619 | 395 | 123 | 31.2 |
| 8 | 0.979 | 229 | 157 | 68.4 |
| 9 | 1.194 | 50 | 23 | 45.2 |
| 10 | 1.342 | 285 | 27 | 9.4 |
| | | | average | 47.75 |
| | | | standard deviation | 28.48 |

It can be seen that the untreated group gave a ratio of 83.3% and the treated group gave a ratio of 47.8%, i.e., treatment resulted in 42.7% reduction of infarction. The result is statistically significant (ANOVA) at p=0.02.

The anti-inflammatory activity of these compounds can be demonstrated as follows.

Anti-inflammatory activity of α-tocopherol analogs

Stimulated human leukocytes release radicals and other oxygen metabolites, which, during inflammation, act as microbicidal agents. At the same time, they release proteolytic enzymes, such as elastase, which are also microbicidal but potentially threaten the connective tissue of the host. An endogenous $\alpha_1$-proteinase inhibitor ($\alpha_1$Pi) normally protects the host tissue from proteolytic digestion. $\alpha_1$Pi is, however, inactivated by the leukocyte-derived oxidants. The inactivation of $\alpha_1$Pi is antagonized by the disclosed radical scavengers 2-(3,4-dihydro-6-hydroxy-2,5,7,8-tetramethyl-2H-1-benzopyran-2-yl)-N,N,N-trimethylethanammonium, 4-methylbenzylsulfonate (Compound A) and 3,4-dihydro-2-(2-dimethylaminoethyl)-2,5,7,8-tetramethyl-2H-1-benzopyran-6-ol (Compound B). The concentration needed to protect 50% of the elastase inhibitory capacity of $\alpha_1$Pi ($PC_{50}$) depends on the amount of stimulated leukocytes present.

TABLE IV

PROTECTION OF $a_1$Pi
FROM LEUKOCYTE-MEDIATED INACTIVATION

| α-tocopherol analog | Relative $PC_{50}$ (μM/μg leukocyte protein) |
|---|---|
| Compound A | 4.5 ± 1* |
| Compound B | 7.3 |
| Trolox | Inactive at 1 mM |

*mean ± S.D. (n = 3)

Method

The procedure described by Skosey and Chow was followed (see Skosey, J. L. and Chow, D. C. (1985) In *Handbook of Methods for Oxygen Radical Research* (Greenwald, R. A., ed.) pp. 413–416, CRC Press, Boca Raton). In short, human $\alpha_1$Pi was incubated with zymosan-stimulated human peripheral-blood leukocytes in the absence or presence of the scavengers. The amount of $\alpha_1$Pi protected from oxidative inactivation was determined by its residual elastase inhibitory capacity.

Relevance to Inflammation

The matter has been reviewed by Weiss (see Weiss, S. J. (1989) *N. Engl. J. Med.* 320, 365–376). Lung emphysema is associated with a genetic defect in $\alpha_1$Pi; the disease is further enhanced by oxidants inhaled during cigarette smoking, which leads to oxidative inactivation of $\alpha_1$Pi in the lung tissue (see Travis, J. and Salvesen, G. S. (1983) *Annu. Rev. Biochem.* 52, 655–709). Oxidized $\alpha_1$Pi has also been isolated from rheumatoid synovial fluid ( see Wong, P. S. and Travis, J. (1980) *Biochem. Biophys. Roc. Commun.* 06, 1440–1454). The degradation of hyaluronic acid, a macromolecule accounting for the viscosity of synovial fluid, is triggered by superoxyl radicals released from human leukocytes in vitro (see Greenwald, R. A. and Moak, S. A. (1986) *Inflammation* 10, 15–30). Furthermore, nonsteroidal anti-inflammatory drugs were shown to inhibit the release of superoxyl radicals from leukocytes (see Strom, H. and Ahnfelt-Ronne,I. (1989) *Agents and Actions* 26, 235–237 and Roch-Arveiller, M. Revelant, V., Pharm Huy, D., Maman, L., Fontagne, J., Sorenson, J. R. J. and Giroud, J. P. (1990) *Agents and Actions* 31, 65–71), and 5-aminosalicylic acid may exert its therapeutic activity in inflammatory bowel disease by a radical scavenger mechanism (see Ahnfelt-Ronne, I., Nielsen, O. H., Christensen, A., Langholz, E., Binder, V. and Riis, P. (1990) *Gastroenterology* 98, 1162–1169). We believe, therefore, that the α-tocopherol analogs may be useful in the mentioned pathologic situations. Inflammatory bowel disease may be a special target because 2-(3,4-dihydro-6 -hydroxy-2,5,7,8-tetramethyl-2H-

1-benzopyran-2-yl)-N,N,N -trimethylethanammonium, 4-methylbenzylsulfonate is not or ally absorbed and is found unchanged in the feces. An immune-stimulatory effect of antioxidants has also been reported in that they enhanced lymphocyte activity (Anderson, R. and Lukey, P. T. (1987) Ann. N.Y. Acad. Sci. 498, 229–247) in vitro in the presence of triggered leukocytes, and ex vivo after pretreatment of human volunteers.

Most preferably, the compounds are administered intravenously particularly under crisis situations wherein it is essential that the therapeutic agent be gotten to its site of action as quickly as possible, such as in those emergency conditions caused by coronary infarction, stroke and surgical interventions, conditions which can cause severe reperfusion damage.

Thus, using standard and well known methodology, as well as by comparison with known compounds found useful, it is to be found that the compounds are free radical scavengers useful in the prevention and treatment of such disease states related to neurotoxicity due to excessive glutamate release, to Huntington's disease, Alzheimer's disease and other cognitive dysfunctions, (e.g., memory, learning and attention deficits), amnesia, and Parkinson's disease, as well as the treatment and prevention of tissue damage in heart, lung, kidney, pancreas, testis following testicular torsion, and brain tissues induced by ischemia/reperfusion, and to allay acute blood loss due to haemorrhagic shock.

The compounds of this invention can be utilized both prophylactically and therapeutically. The amount of active ingredient for therapeutic administration can vary over a wide range and is dependent upon such factors as the species of mammal to be treated, its age, health, sex, weight, nature and the severity of the condition being treated. Generally, a therapeutically effective amount of the active ingredient to be administered will range from about 0.1 mg/kg to 50 mg/kg of body weight per day. For prophylactic administration, corresponding lower doses can be utilized.

The compounds of this invention can, in many instances, be orally administered, preferably using more active ingredient per day than when parenterally administered, preferably taking divided doses 3 to 4 times per day. Some of the compounds of formula 1 such as 3,4-hydro-6-hydroxy-N,N,N,2,5,7,8-heptamethyl-2H-1-benzopyran-2-ethanaminium 4-methylbenzenesulfonate, have been found to be not orally absorbed and thus alternate means of administration are preferred for such compounds. Preferably, enteral administration in post "crisis" situations, particularly after release from hospitalized conditions. The compounds can be used in standard dosage unit forms such as tablets, capsules, dragees, lozenges, elixirs, emulsions, suspensions, and in cases wherein topical application is preferred by suppository or sublingual administration. Tablets and capsules containing from 100 to 400 mg of active ingredient are preferred modes of enteral administration. Of course, in the treatment of inflammation the preferred method of administration is by depot injection directly to the situs of the inflammation area with follow-up enteral means of administration.

In preparing solid dose forms such as tablets, the active ingredient is generally blended with conventional pharmaceutical carriers or excipients such as gelatin, various starches, lactose, calcium phosphate or powdered sugar. The term pharmaceutical carrier as used herein also includes lubricants employed to improve the flow of tablet granulations and which prevent adhesion of tablet material to the surfaces of tablet dies and punches. Suitable lubricants include, for example, talc stearic acid, calcium stearate, magnesium stearate and zinc stearate. Also included within the definition of a pharmaceutical carrier as used herein, are disintegrating agents added to assist the breakup and dissolution of tablets following administration, as well as coloring and/or flavoring agents to enhance the aesthetic qualities of the tablets and make them more acceptable to the patient.

Suitable liquid excipients for the preparation of liquid dosage unit forms include water and alcohols such as ethanol, benzyl alcohol and the polyethylene glycols, either with or without the addition of a surfactant. In general, the preferred liquid excipients, particularly for injectable preparations, include water, physiological and saline solutions, dextrose and glycol solutions such as an aqueous propylene glycol or polyethylene glycol solutions. In order to minimize or eliminate irritation at the site of injection, such compositions may contain a non-ionic surfactant having a hydrophile-lipophile balance (HLB) of from about 12 to about 17. The quantity of surfactant in such formulations ranges from about 5 to 15% by weight. The surfactant can be a single component having the above-identified HLB, or a mixture of two or more components having the desired HLB. Illustrative of surfactants useful in parenteral formulations are the class of polyoxyethylene sorbitan fatty acid esters as, for example, sorbitan monooleate and the high molecular weight adducts of ethylene oxide with a hydrophobic base, formed by the condensation of propylene oxide with propylene glycol. In certain topical and parenteral preparations, various oils can be utilized as carriers or excipients. Illustrative of such oils are mineral oils, glyceride oils such as lard oil, cod liver oil, peanut oil, sesame oil, corn oil and soybean oil. For insoluble compounds, suspending agents may be added as well as agents to control the viscosity, as for example,magnesium aluminum silicate or carboxymethyl-cellulose. In addition to these excipients, buffers, preservatives and emulsifying agents may also be added. Typical enema preparation of the retention type enema utilize small volumes, generally much less than about 150 ml for an adult, typically volumnes of only a few milliliters are preferred. Excipients and solvents for use in retention enemas should, of course, be selected so as to avoid colonic irritation and should also be selected so as to minimize absorption of the various agents.

Of course, as is true in most instances wherein certain classes of chemical compounds have been found to have beneficial therapeutic end-use applications, certain sub-generic groups and certain specific compounds are preferred. In this instance the preferred compounds of Formula I are those wherein $R_5$, $R_7$ and $R_8$ are methyl; wherein $R_6$ is formyl, methyl carbonyl, t-butylcarbonyl, ethylcarbonyl, propylcarbonyl, pentylcarbonyl; wherein n is 2 (representing an ethylene moiety), and $R_1$, $R_2$ and $R_3$ are methyl, the preferred anions are chloro, bromo or p -toluenesulfonyl. Preferred specific compounds are those compounds comprised of the foregoing preferred groups, particularly 2-(3, 4-dihydro-6-hydroxy-2,5,7,8-tetramethyl-2H-1-benzopyran-2-yl) ethyl-N,N,N-trimethylammonium bromide also referred to as 3,4-dihydro-6-hydroxy-N,N,N,2,5,7,8-heptamethyl-2H-1-benzopyran-2-ethanaminium bromide and its individual (R) and (S) isomers; 3,4-dihydro-6-hydroxy-N,N,N,2,5,7,8-heptamethyl-2H-1-benzopyran-2-ethanaminium 4-methylbenzenesulfonate and its individual (R) and (S) isomers; 2-(3,4-dihydro-2,5,7,8-tetramethyl-6-methylcarbonyloxy-2H-1-benzopyran-2-yl)ethyl-N,N,N-trimethylammonium bromide, and 2-(3,4-dihydro-2,5,7,8-tetramethyl-6-methylcarbonyloxy-2H-1-benzopyran-2-yl)ethyl-N,N,N-trimethylammonium p-toluenesulfonate.

Of course, it is obvious that the 2-position methyl moiety may be removed or replaced with another lower alkyl (e.g., the 2-position methyl may be replaced with H, ethyl, propyl, butyl and the like). Such so-modified compounds are also contemplated within the scope of this invention for the utilities herein alleged, and may be prepared by standard procedures obvious to those skilled in the art.

What is claimed is:

1. A compound of the formula $$\text{R}_6\text{O} \underset{\underset{\text{R}_8}{\overset{}{|}}}{\overset{\overset{\text{R}_5}{|}}{\bigcirc}} \text{R}_7 \quad \text{O} \overset{\text{R}_3}{\underset{\text{CH}_3}{|}} (\text{CH}_2)_n \text{N}^\oplus - \text{R}_2 \cdot \text{X}^\ominus$$
I the (R) and (S) enantiomers and racemic mixtures thereof wherein $R_1$, $R_2$ and $R_3$, each individually is a $C_{1-6}$ lower alkyl, X is a halide or $R_4 SO_3^\ominus$ with $R_4$ being H, $C_{1-6}$ alkyl, aryl, or aralkyl, $R_5$ is H or $C_{1-6}$ alkyl, $R_6$ is H or —C(O)R, R being H or $C_{1-9}$ alkyl, $R_7$ is H or $C_{1-6}$ alkyl, $R_8$ is H or $C_{1-6}$ alkyl and n is an integer of 1 to 6.

2. A compound of claim 1 wherein $R_5$, $R_7$ and $R_8$ are methyl.

3. A compound of claim 1 wherein $R_1$, $R_2$ and $R_3$ are methyl.

4. A compound of claim 1 wherein X is chloro, bromo or p-toluenesulfonyl.

5. A compound of claim 1 wherein $R_6$ is H.

6. A compound of claim 1 wherein $R_6$ is R—C(O).

7. A compound of claim 1 wherein n is 2.

8. A compound of claim 2 wherein $R_1$, $R_2$ and $R_3$ are methyl.

9. A compound of claim 8 wherein $R_6$ is H.

10. A compound of claim 8 wherein $R_6$ is R—C(O).

11. A compound of claim 9 wherein n is 2.

12. A compound of claim 9, said compound being 2-(3,4-dihydro-6-hydroxy-2,5,7,8-tetramethyl-2H-1-benzopyran-2-yl)ethyl-N,N,N-trimethylammonium bromide.

13. A compound of claim 9, said compound being 3,4-dihydro-6-hydroxy-N,N,N,2,5,7,8-heptamethyl-2H-1-benzopyran-2-ethanaminium 4-methylbenzenesulfonate.

14. A compound of claim 9, said compound being (R)-3,4-dihydro-6-hydroxy-N,N,N,2,5,7,8-heptamethyl-2H-1-benzopyran-2-ethanaminium 4-methylbenzenesulfonate.

15. A compound of claim 9, said compound being (S)-3,4-dihydro-6-hydroxy-N,N,N,2,5,7,8-heptamethyl-2H-1-benzopyran-2-ethanaminium 4-methyl benzenesulfonate.

16. A compound of claim 10, said compound being 2-(3,4-dihydro-2,5,7,8-tetramethyl-6-methylcarbonyloxy-2H-1-benzopyran-2-yl)ethyl-N,N,N-trimethylammonium bromide.

17. A compound of claim 10, said compound being 2-(3,4-dihydro-2,5,7,8-tetramethyl-6-methylcarbonyloxy-2H-1-benzopyran-2-yl)ethyl-N,N,N-trimethylammonium p-toluenesulfonate.

18. A method for preventing or treating injury caused by reperfusion of an ischemic tissue in a patient in need thereof which comprises administering to the patient an effective amount of a compound of one of claims 11–17.

19. A method for treating inflammatory bowel disease in a patient in need thereof which comprises administering to the patient an effective amount of a compound of one of claims 11–17.

20. A method for treating inflammatory bowel disease in a patient in need thereof which comprises administering to the patient an effective amount of a compound of claim 14.

21. A method for preventing or treating injury caused by reperfusion of an ischemic tissue in a patient in need thereof which comprises administering to the patient an effective amount of a compound of claim 13.

22. A method for preventing or treating injury caused by reperfusion of an ischemic tissue in a patient in need thereof which comprises administering to the patient an effective amount of a compound of claim 14.

23. A method for preventing or treating injury caused by reperfusion of an ischemic tissue in a patient in need thereof which comprises administering to the patient an effective amount of a compound of claim 15.

24. A method for treating inflammatory bowel disease in a patient in need thereof which comprises administering to the patient an effective amount of a compound of claim 13.

25. A method for treating inflammatory bowel disease in a patient in need thereof which comprises administering to the patient an effective amount of a compound of claim 15.

* * * * *

UNITED STATES PATENT AND TRADEMARK OFFICE
CERTIFICATE OF CORRECTION

PATENT NO. : 5,500,444

DATED : March 19, 1996

INVENTOR(S) :
J. Martin Grisar, et al.

It is certified that error appears in the above-identified patent and that said Letters Patent is hereby corrected as shown below:

At column 2, line 14, the patent reads "carbons atoms" and should read --carbon atoms--.
At column 7, line 50, the patent reads "pyran2yl)" and should read --pyran-2-yl)--.
At column 10, line 6, the patent reads "H2O" and should read --$H_2O$--.
At column 10, line 30, the patent reads "yeld" and should read --yield--.
At column 10, line 30, the patent reads "C./100 tort" and should read --C/100 torr--.
At column 10, line 58, the patent reads "C./1 tort" and should read --C/1 torr-- .
At column 11, line 5, the patent reads "N,,N,N" and should read --N,N,N-- .
At column 11, line 40, the patent reads "UV ($H_2$))" and should read --UV ($H_2O$)--.
At column 16, lines 1-2, the patent reads "52-67-15" and should read --52-67-5--.
At column 16, line 14, the patent reads "8tetramethyl" and should read --8-tetramethyl--.
At column 16, line 17, the patent reads "3,4dihydro" and should read --3,4-dihydro--.
At column 19, line 2, the patent reads "or ally" and should read --orally-- .
At column 20, line 39, the patent reads "volumnes" and should read --volumes--.

Signed and Sealed this

Seventh Day of April, 1998

Attest:

BRUCE LEHMAN

Attesting Officer

Commissioner of Patents and Trademarks